(12) United States Patent
Den Hartog et al.

(10) Patent No.: US 8,257,403 B2
(45) Date of Patent: Sep. 4, 2012

(54) ORTHOPEDIC PLATE FOR USE IN THE MIDFOOT

(75) Inventors: Bryan D Den Hartog, Rapid City, SD (US); Dustin Ducharme, Stow, OH (US)

(73) Assignee: Orthohelix Surgical Designs, Inc., Medina, OH (US)

( * ) Notice: Subject to any disclaimer, the term of this patent is extended or adjusted under 35 U.S.C. 154(b) by 467 days.

(21) Appl. No.: 12/378,540

(22) Filed: Feb. 17, 2009

(65) Prior Publication Data

US 2009/0210011 A1   Aug. 20, 2009

Related U.S. Application Data

(60) Provisional application No. 61/066,185, filed on Feb. 19, 2008.

(51) Int. Cl.
*A61B 17/80* (2006.01)
(52) U.S. Cl. ........ 606/280; 606/906; 606/281; 606/286; 606/289
(58) Field of Classification Search .......... 606/280–299, 606/70, 71
See application file for complete search history.

(56) References Cited

U.S. PATENT DOCUMENTS

| | | | |
|---|---|---|---|
| 4,219,015 | A | 8/1980 | Steinemann |
| 4,493,317 | A | 1/1985 | Klaue |
| 449,692 | A1 | 10/2001 | Michelson |
| D449,692 | S | 10/2001 | Michelson |
| 6,565,571 | B1 | 5/2003 | Jackowski et al. |
| 6,576,018 | B1 | 6/2003 | Holt |
| 6,623,486 | B1 * | 9/2003 | Weaver et al. ............... 606/281 |
| 7,052,499 | B2 | 5/2006 | Steger et al. |
| 7,108,697 | B2 | 9/2006 | Mingozzi et al. |

(Continued)

FOREIGN PATENT DOCUMENTS

JP   20030102744   4/2003

(Continued)

OTHER PUBLICATIONS

Foot Reconstructive and Trauma Surgery—Internal and External Fixation Systems May 29, 2008 (pp. 2-12).

(Continued)

*Primary Examiner* — Thomas Barrett
*Assistant Examiner* — Melissa A Golob
(74) *Attorney, Agent, or Firm* — Hudak, Shunk & Farine Co. LPA

(57) ABSTRACT

An orthopedic plate is specifically configured for implantation at the mid-foot. The plate has a first radius along the x-axis in the y direction and a second radius along the y-axis in the y direction The plate has an ring-shaped footprint with two diagonal sets, (one set of longer and one set of shorter) of opposing tabs. In each set of tabs, one tab includes a compression slot that extends and causes compression in a direction toward a screw hole in the opposing tab of the other set of tabs. The maximum length of the plate extends between the longer set of tabs, and an opening is included along this axis to allow viewing of the bone/bone fragments under the plate. The placement of the compression slots and the screw holes account for the progressively anterior placement of the cuneiforms and provides for compression in the medial direction. In a further embodiment, the plate is flat or includes a crease midway between the first and second tabs, which facilitates placement of the plate at the joint between the metatarsals and the cuneiforms.

17 Claims, 3 Drawing Sheets

U.S. PATENT DOCUMENTS

| | | |
|---|---|---|
| 7,189,237 B2 | 3/2007 | Huebner |
| 2001/0047172 A1* | 11/2001 | Foley et al. .............. 606/69 |
| 2005/0059971 A1* | 3/2005 | Michelson .............. 606/69 |
| 2006/0015102 A1 | 1/2006 | Toullec et al. |
| 2006/0025772 A1* | 2/2006 | Leibel et al. .............. 606/69 |
| 2006/0081553 A1 | 4/2006 | Patterson et al. |
| 2006/0106387 A1 | 5/2006 | Fanger et al. |
| 2006/0173459 A1* | 8/2006 | Kay et al. .............. 606/69 |
| 2006/0235396 A1 | 10/2006 | Sanders et al. |
| 2006/0235397 A1 | 10/2006 | Sanders et al. |
| 2006/0241592 A1 | 10/2006 | Myerson et al. |
| 2006/0241607 A1 | 10/2006 | Myerson et al. |
| 2006/0241608 A1 | 10/2006 | Myerson et al. |
| 2007/0016205 A1 | 1/2007 | Beutter et al. |
| 2007/0073298 A1 | 3/2007 | Beutter et al. |
| 2007/0083204 A1 | 4/2007 | Sidebotham |
| 2007/0233114 A1 | 10/2007 | Bouman |

FOREIGN PATENT DOCUMENTS

JP        20060280951        10/2006

OTHER PUBLICATIONS

New Trauma Products from AO Development, Jun. 2006 (pp. 1-8).

A Straight Answer for Kids, Jan. 2007 (4 pages).

VariAx Foot Locking Plate System by Stryker dated 2009 (23 pages).

The corresponding International Search Report and Written Opinion dated Mar. 27, 2009.

Diamond Carpal Fusion Plate Surgical Plate by Small Bone Innovations (13 pages), dated 1991.

* cited by examiner

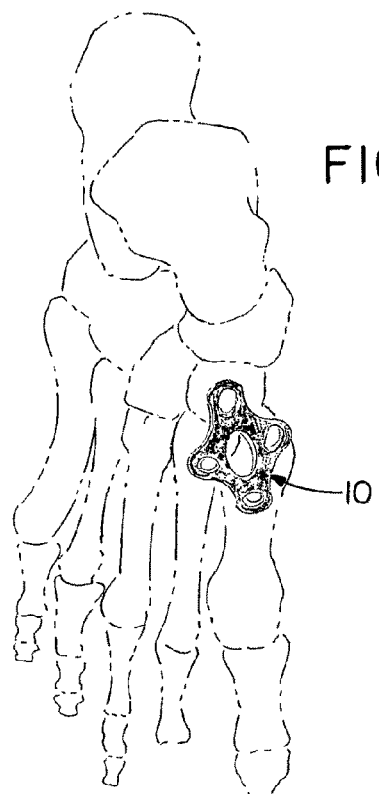
FIG.-1
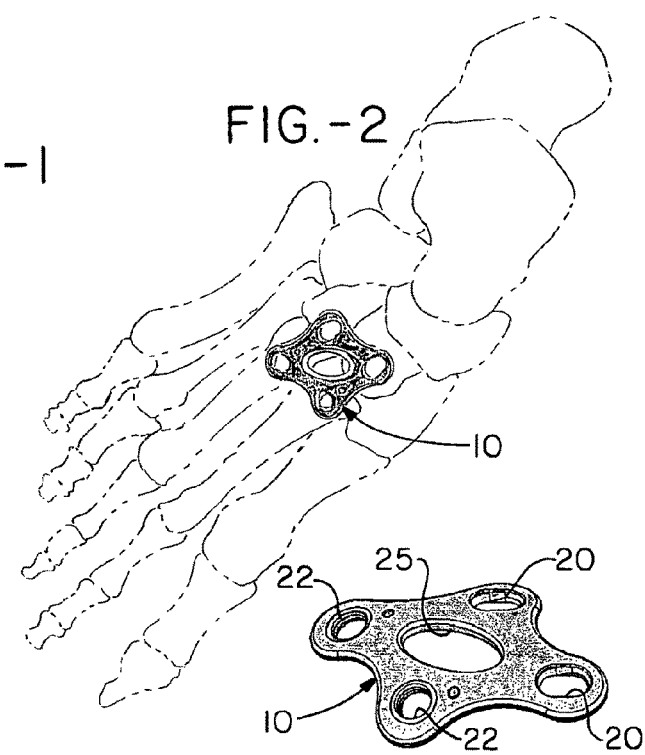
FIG.-2
FIG.-3
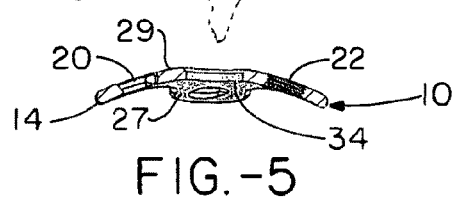
FIG.-5
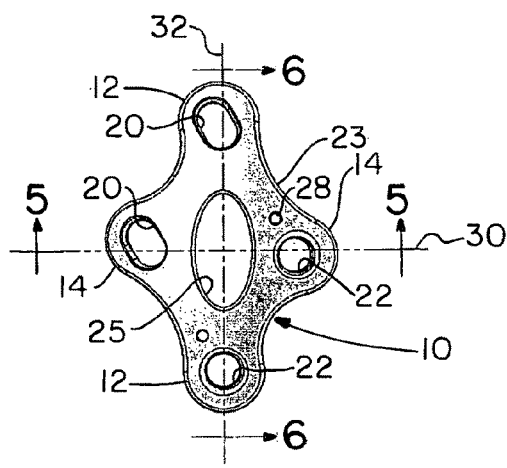
FIG.-4
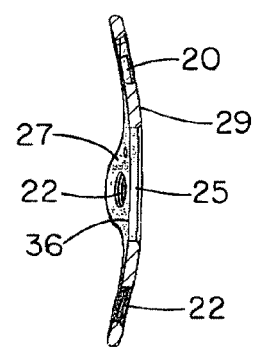
FIG.-6

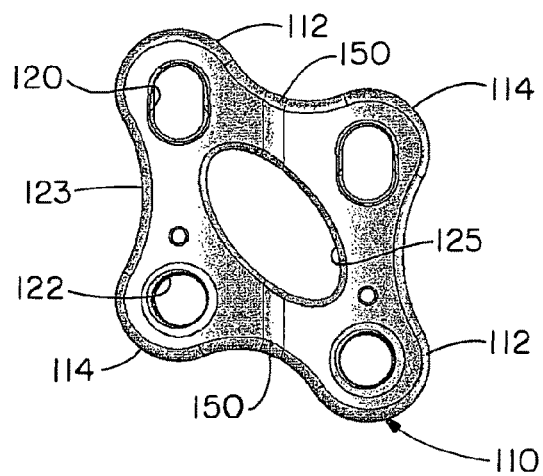
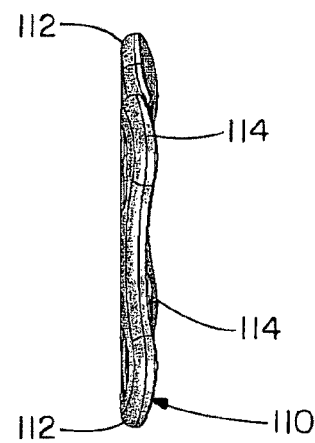
FIG.-7     FIG.-8
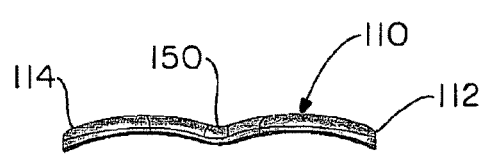
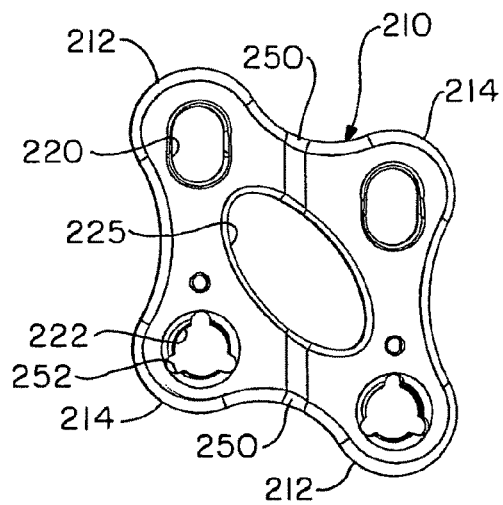
FIG.-9
FIG.-10
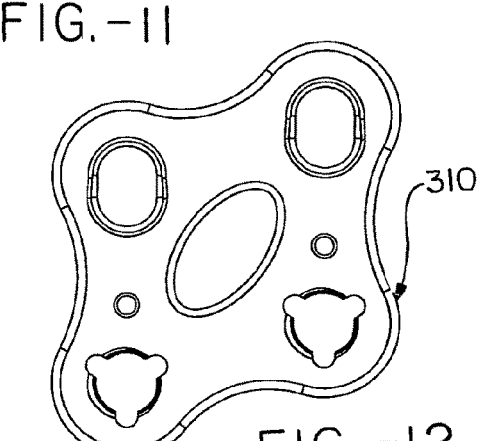
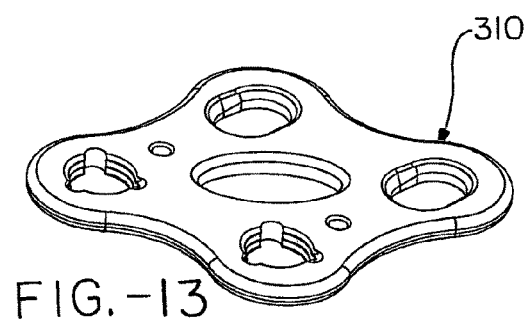
FIG.-11
FIG.-12     FIG.-13

ORTHOPEDIC PLATE FOR USE IN THE MIDFOOT

CROSS-REFERENCE

This is a U.S. patent application of U.S. Provisional Application No. 61/066,185 filed on Feb. 19, 2008 for ORTHOPEDIC PLATE FOR USE IN THE MIDFOOT which is hereby fully incorporated by reference.

FIELD OF THE INVENTION

The present invention relates to an orthopedic plate which is configured for the fixation of the bones of the midfoot including, for example, stabilization of a fracture, dislocation or reconstruction of a deformity.

BACKGROUND OF THE INVENTION

Together the foot and ankle have over 25 bones and 33 joints along with more than 100 named muscles, tendons, and ligaments and a network of blood vessels, nerves, all residing beneath a relatively slim covering of soft tissue and skin. Structurally, the foot has three main anatomical regions: the forefoot, the midfoot, and the hindfoot. These parts work together with the ankle, to provide the body with support, balance, and mobility. A structural flaw or malfunction in any one part can result in the development of problems, which are manifested in other areas of the body.

The forefoot includes the five toes (which are also known as the "phalanges") and their connecting long bones (or "metatarsals"). Several small bones together comprise a phalanx or toe. Four of the five toes have three phalanx bones respectively connected by two joints. The big toe (or "hallux") has two phalanx bones distal and proximal with a joint in between called the interphalangeal joint. The big toe articulates with the head of the first metatarsal at the first metatarsophalangeal joint (the "MTP" joint) and there are two tiny, round bones called sesamoids on the plantar side of the metatarsal head. The phalanges are connected to the metatarsals at the ball of the foot. The forefoot balances pressure on the ball of the foot and bears a substantial amount of the body weight.

The bones of the midfoot from medial to lateral are the $1^{st}$ through $3^{rd}$ cuneiform, the cuboid, and the crescent shaped navicular bone posterior to the cuneiforms, which also forms a joint with the talus that forms the basis for the ankle joint at the hinged intersection of the tibia, the fibula, and the foot The five tarsal bones of the midfoot act together form a lateral arch and a longitudinal arch which help to absorb shock. The plantar fascia (arch ligament) underlays the bones of the midfoot and along with muscles, forms a connection between the forefoot and the hindfoot. The toes and their associated midfoot bones form the first through fifth rays beginning with the great toe as the first ray.

The hindfoot is composed of three joints (subtalar, calcaneocuboid & talonavicular) and links the midfoot to the ankle. The heel bone (or "calcaneus") projects posteriorly to the talus and forms a lever arm to activate the hinged action of the foot so as to allow propulsion of the entire body from this joint. The calcaneus is joined to the talus at the subtalar joint.

The mid-foot is often the subject of trauma such as results from falls, vehicle crashes and dropped objects. These accidents often result in severe fractures and/or dislocations. A common midfoot fracture is the Lisfranc injury which was identified by a French doctor in the Napoleonic Wars. It commonly occurred when a cavalier fell from his horse with his foot caught in his stirrup and resulted in the fracture and dislocation of multiple bones of the midfoot. A Lisfranc injury has come to indicate an injury to the normal alignment of the cuneiforms and metatarsal joints with the loss of their normal spatial relationships. These types of injuries may occur from dropping a heavy object on the top of the foot or stepping on an uneven surface and falling with the foot in a twisted position. These fractures also occur in athletes when the foot is bound to an article of sports equipment such as skis or snowboards or when the foot is subject to simultaneous impact and rotation, such as skating or ballet jumps or soccer.

A common Lisfranc injury occurs at the joint primarily involving the 1st and 2nd metatarsals and the medial cuneiform. Normal alignment of the joints is lost if the ligaments are disrupted and the bones separate between the medial and mid-cuneiforms or between the 1st, 2nd metatarsal and the medial cuneiform. Failure to treat such an injury may result in joint degeneration and subsequent damage to the adjacent nerves and blood vessels.

Typical surgical treatment of the midfoot re-establishes the normal anatomy of the mid-foot while the fractured bones mend. In some cases, fusion of the joint between the first and second metatarsals and the middle and/or internal cuneiforms may be necessary, for example, where arthritis arises in patients with a prior Lisfranc or similar injury. One current surgical treatment of this injury requires that pins, wires and/ or screws be inserted to stabilize the bones and joints and hold them in place until healing is complete. For example, a pin or screw may be introduced medially into the internal cuneiform and through the base of the second metatarsal bone. While the use of k-wires, pins, and screws may provide acceptable results for younger and more plastic patients, these methods of fixation are not always satisfactory.

SUMMARY OF THE INVENTION

In accordance with the present invention an orthopedic plate is provided that is specifically configured for implantation at the mid-foot and more specifically is configured for the first and second ray or for the second and third ray. The plate has a first and larger radius in the saggital plane and a secondary and lesser radius in the coronal plane resulting in a plate in a first embodiment has the contour of a segment of a torroid. The plate has an amoeboid, or rhomoid footprint which is a modified oval ring with two sets of diagonally opposed tabs. In each set of tabs, one tab includes a compression slot that is an obround that extends in a direction toward a screw hole in the opposing tab of the other set of tabs. The compression slot includes an incline along the lateral edges of the slot that slops downward toward the opposing locking slot (and which is angled relative to the thickness of the slot in the torroidal version of the plate to accommodate the contouring of the plate.) The maximum length of the plate extends between the longer set of tabs, and an opening is included along this axis to allow viewing of the bone/bone fragments under the plate during surgery, but mainly to evaluate fusion radiographically post-operatively. A shorter set of tabs define a second axis which intersects the first axis at its midpoint. The placement of the compression slots and the screw holes account for the posterior placement of the $2^{nd}$ (or middle or intermediate) cunieform relative to the $1^{st}$ (or medial) and $3^{rd}$ (or lateral) cunieform of the cuneiforms and provides for compression in the anterior-posterior direction; namely between the metatarsal and cuneiform. In a second embodiment, the footprint (i.e. the top profile) is the same, but the plate is planar.

In a third embodiment the top outline or profile remains the same, but the plate includes a "crease" or rib which dissects the plate into two sets of a locking hole and a compression slot. The crease midway between the first and second arms facilitates placement of the plate at the joint between adjacent rays.

BRIEF DESCRIPTION OF THE DRAWINGS

FIG. 1 is a dorsal view of a mid-foot with an orthopedic plate in accordance with a first embodiment of the invention is positioned for the first and second ray;

FIG. 2 is a dorsal view of a mid-foot with an orthopedic plate in accordance with a first embodiment of the invention is positioned for the second and third ray;

FIG. 3 is a perspective view of the orthopedic plate shown in FIGS. 1 and 2;

FIG. 4 is a top view of the orthopedic plate of FIGS. 1 and 2;

FIG. 5 is a first cross-sectional view of the plate shown in FIG. 1, taken along line 5-5;

FIG. 6 is a second cross-sectional view of the plate shown in FIG. 2;

FIG. 7 is top view of a further embodiment of an orthopedic plate in accordance with the invention;

FIG. 8 is a first side view of the plate shown in FIG. 7; and

FIG. 9 is a second side view of the plate shown in FIG. 7, taken 90° to the view of FIG. 8;

FIG. 10 is a top view of a further embodiment of the invention;

FIG. 11 is a side view of the embodiment shown in FIG. 10;

FIG. 12 is a perspective view of the embodiment shown in FIG. 10;

FIG. 13 is a side perspective view of the embodiment shown in FIG. 12; and,

DETAILED DESCRIPTION OF THE INVENTION

Figure 14:
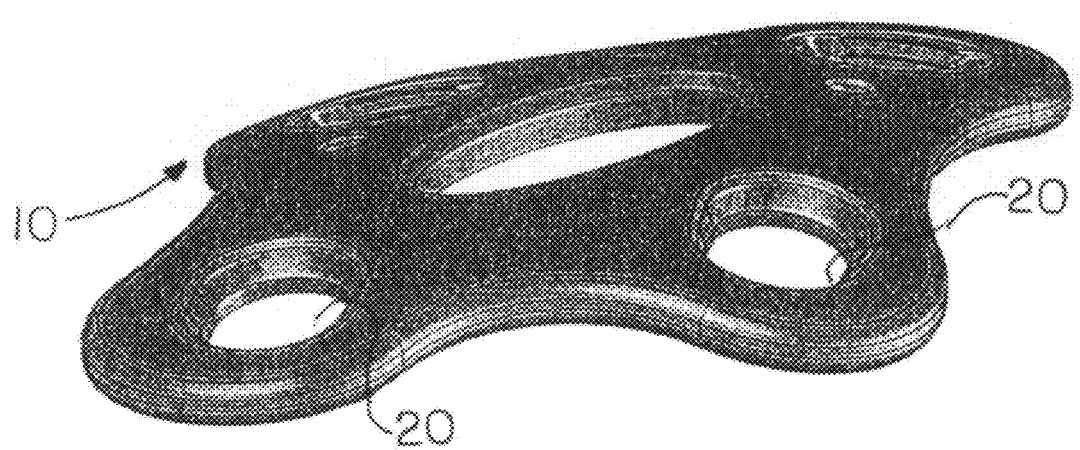
FIG. 14 is side perspective view of the embodiment shown in FIG. 3 showing a detail of the compression slots.

FIG. 1 shows a skeletal version of a foot from the top (i.e. the dorsal view) with the midfoot plate 10 of the present invention in place between the junction of the first and second metatarsals and the first and second cuneiforms (i.e. the medial and intermediate cuneiforms). Thus, FIG. 1 illustrates the plate used in fixation of the bones of the first and second ray or 1-2 TMT joint complex ($1^{st}$ tarso-metatarsal joint and $2^{nd}$ tarso-metatarsal joint). The plate can also be used for fixation of the second and third ray (or 2-3 TMT joint complex), i.e. at the base of the second and third metatarsal and the junction of the second and third cuneiforms (i.e. intermediate and lateral cuneiforms) as in shown in FIG. 2.

As viewed from the top in FIG. 3, it can be seen that the plate 10 has two sets of opposing tabs that are slightly offset from each other so as to define a kind of amemboid shape (i.e. a rhomoid with curving lateral edges that form rounded tabs at the corners). The outline or profile can also be viewed as a modified ring having a first set of diagonally opposed longer tabs 12 and a second set of diagonally opposed shorter tabs 14. Each 16, 18 of one of the longer and the shorter tabs include a compression slot 20, and the other of the pair of tabs includes a screw hole 22 (which can include internal threads so as to form a locking interface with the respective bone or bone fragment.) Alternatively, the screw hole can accommodate other screw/plate interfaces such as a variable locking mechanism to allow the screw to be placed with the axis at a variety of angles relative to the plate and to be subsequently locked into position. One such mechanism is a bushing which is rounded on the outside to swivel in the correspondingly rounded plate hole and which has a locking interface with the head of the locking screw including, for example, mating threads, cams or grooves. The plate includes incurvatures 23 between the tabs to minimize the material used and maximize the fit. At the intersection of the tabs, the plate includes an opening 25 which can be used to view the placement of the plate relative to the bones as well as for adding bone graft material. The opening is preferably an oval shape, which allows the maximization of the area viewed while maintaining sufficient stiffness to hold the bones in position to allow fusion.

FIGS. 4 and 5 illustrate the plate in cross-section along a first axis and a perpendicular axis. As can be seen the plate has a generally uniform thickness between the inward surface 27 which opposes and optimally, but not necessarily engages the bones, and the outward surface 29. In addition, while the inward surface 27 of the plate 10 includes a generally uniform radius of curvature 34, 36 along both the first 30 and the second axis 32, the radii of these two curves differ (specifically the radius of the first curvature 34 is from about 50 to about 90, more preferably about 60 to about 80, and most preferably about 65 to about 75 millimeters, while the radius of the second curvature 35 is from about 10 to about 50, more preferably about 20 to about 40, and most preferably about 25 to about 35 millimeters. The first radius is from about 1 to about 4 times that of the second radius, and more preferably about 1.5 to about 3 times that of the second. Thus, the plate has the shape of a segment of a torroid which maximizes the ability to place the plate as desired without the need for additional pre-surgical contouring, although the plate thickness allows for bending if necessary. In a second embodiment shown in FIGS. 11-13, the plate 310 has the same footprint, but is planar or flat.

In one method of causing locking of the screw relative to the plate, the screw could include external screw threads that mate with internal threads in the locking screw hole at a pre-selected angle, in this instance, the screw axis is perpendicular to a tangent at the top of the screw hole so that the screw axis angles slightly toward the bottom of the plate. The screw used in the compression slot has a rounded rear shoulder (such as a hemisphere, or a torroid) which mates with the concavely rounded groove of the compression slot. The lateral edge of the compression slot further includes an inclined shoulder as shown in FIGS. 13 and 14 that slope downward toward the bone-contacting surface of the plate in the direction of the corresponding lock hole. The shoulder is engaged by the screw head to cause the translation of force from a downward force to a force that includes a longitudinal component.

The screws useful with the plate of the present invention are self-starting, self-tapping screws including the option of partial or full cannulation. The screws include a cutting end having multiple flutes, and preferably 2 or 3 flutes about a conical recess. The screws further include a partial taper of the inner diameter in the proximal end over the first several thread turns, for example over 2-8, and preferably over 3-5 turns in order to increase the fatigue life of the screw as well as providing potential physiological advantages in use. The screws further include a torque driving recess.

The plate is formed of a biocompatible material, and preferably a metal such as surgical grade stainless steel, titanium or a titanium alloy. Preferably, the plate has a thickness of between about 1.0 and 2.0 millimeters, more preferably between about 1.25 and 1.75 millimeters, and most preferably between about 1.4 and 1.6 millimeters. The plate includes a continuous outer edge 40 which is defined between the top and the bottom surface and a continuous inner edge 42 which is defined as the periphery of the opening 25.

In addition, the plate 10 can include a small through hole 28 sized to receive a K-wire or other similar guide wire.

Further embodiments of the plate 110 (210) are shown in FIGS. 7-9, and 10 (which is the same as in FIGS. 7-9 but includes guide keyways). These embodiments include a similar peripheral shape as the first embodiment, with two sets of opposing diagonal tabs that are slightly offset from each other so as to define a kind of ring having a first set of diagonally opposed longer tabs 112 (212) and a second set of diagonally opposed shorter tabs 114 (214). Again, each of the set of longer and shorter tabs include a compression slot 120 (220), and the other of the pair of tabs includes a screw hole 122 (222) (which can include internal threads so as to form a locking interface with the respective bone or bone fragment.) The plate includes incurvatures 123 between the tabs to minimize the material used and maximize the fit. At the intersection of the tabs, the plate includes an opening 125 (225) which can be used to view the placement of the plate relative to the bones as well as for adding bone graft material. This embodiment of the plate 110 includes a crease 150 which helps to define the placement of the plate relative to the junction of adjacent rays. The locking holes 222 include guide grooves 252 for a drill guide.

The crease 150 is perhaps better viewed in FIG. 7 which shows the plate from the side.

During the surgery the joints are first prepped which may include de-articulation between the four bones to be fused. The plate is placed and held in place via k-wire (thru specific hole) or olive wire (thru compression slot). The plate is located such that all of the screws are aimed into the targeted bones and away from the joint. The two locking screws are screwed into adjacent cunieforms. The first compression screw is put into the metatarsal head and the second compression screw is put into the adjacent metatarsal head. The pins and wires are removed, and the plate is viewed radiographically. The incision is closed per the usual method.

While in accordance with the patent statutes the best mode and preferred embodiment have been set forth, the scope of the invention is not limited thereto, but rather by the scope of the attached claims.

What is claimed is:

1. A plate system which is capable of fixation of bone at the first and second or the second and third ray of the midfoot comprising a first and a second locking screw, a first and a second non-locking screw each having a head, and a plate having a top surface and a bone facing surface and having a first plate portion extending along a first length defining a first longitudinal axis and having a first end and a second end, the first end having a first terminal tab with a first compression slot having a first long axis and the second end including a second terminal tab with a first locking hole having a midpoint and a first midline, and the plate having a second plate portion extending along a second length defining a second longitudinal axis and having a third end and a fourth end, the third end having a third terminal tab along the second length with a second compression slot having a second long axis and the fourth end including a fourth terminal tab with a second locking hole having a midpoint and a second midline, each of the first and the second compression slots defining a first lateral edge and a second lateral edge which each include an inclined shoulder that slopes downward toward the bone facing surface of the plate parallel to the respective long axis of the respective compression slot, the midline of the first locking hole and the long axis of the first compression slot being aligned along the first longitudinal axis of the plate, the midline of the second locking hole and the long axis of the second compression slot being aligned along the second longitudinal axis of the plate, and the inclined shoulders of the each compression slot being engaged by a respective non-locking screw head to cause the translation of the respective non-locking screw along the respective long axis of the respective slot and towards the respective locking hole to cause compression in the direction of the respective long axis in the associated bone toward the respective locking hole in use, and a line connecting the midpoint of the first locking hole and the second locking hole being other than perpendicular to the first or second longitudinal axis.

2. A plate as set forth in claim 1 wherein the bone facing surface of the plate has an inner surface which defines a first radius along the first length and a second radius along the second length.

3. A plate as set forth in claim 1 wherein the plate further includes a central opening.

4. A plate as set forth in claim 3 wherein the central opening is an oval.

5. A plate as set forth in claim 1 wherein the contour of the plate forms a segment of a torroid.

6. A plate as set forth in claim 1 wherein the plate is planar.

7. A plate as set forth in claim 1 wherein the plate includes a crease.

8. A plate system for use in associated bone comprising a plate having a top surface and a bone-facing surface and a profile which comprises a first lateral side joined to a second lateral side, and at least one locking screw and at least one non-locking screw for each of the first lateral side and the second lateral side, each of the first side and the second side comprising a first end with a rounded tab and a second end with a rounded tab aligned along a respective longitudinal axis, each of the first end and the second end joined by a middle section, each of the first ends including a locking hole for the locking screw and the locking hole having a midpoint and a midline, and each of the second ends including a compression slot having a long axis, each of the compression slots defining a first lateral edge and a second lateral edge which include an inclined shoulder that slopes downward toward the bone facing surface of the plate parallel to the long axes of the respective compression slot, the midline of the respective locking hole and the long axis of the respective compression slot being aligned along the respective longitudinal axis of the first and second lateral side of the plate, each of the non-locking screws having a head and the inclined shoulders of the compression slots being engaged by the respective non-locking screw heads to cause the translation of the non-locking screws along the long axes of the slots and towards the respective locking hole to cause compression in the direction of the respective long axis in the associated bone toward the respective locking hole in use, and a line connecting the midpoint of the first locking hole and the second locking hole being other than perpendicular to the first or second longitudinal axis.

9. A plate system as set forth in claim 8 wherein each of the first and the second tabs comprise a portion of a circle.

10. A plate system as set forth in claim 9 wherein each of the middle sections has a width perpendicular to the respective longitudinal axis which is smaller that the diameter of either the first tab circle or the second tab circle.

11. A plate system as set forth in claim 8 wherein the plate has a generally uniform thickness between the top surface and the bone-facing surface.

12. A plate system as set forth in claim 11 wherein the plate includes a radius of curvature toward the bone-facing surface of the plate.

13. A plate system as set forth in claim 12 wherein the plate is a section of a torroid.

14. A plate system as set forth in claim 8 wherein the system further includes a drill guide which interacts with the locking hole to allow a pilot hole to be drilled in the associated bone at a desired angle.

15. A plate system as set forth in claim 14 wherein the drill guide includes guides and the locking hole includes grooves which capture the guides to fix the angle of the drill guide.

16. A method of fusing bones, comprising:
surgically accessing a bone,
selecting a plate which has a top surface and a bone-facing surface and a profile with bilateral mirror symmetry, the profile comprising a first lateral side and a second lateral side, each of the first lateral side and the second lateral side having first end which is a tab having a curved portion having a first diameter and a second end which is a tab having a curved portion having a second diameter which may be the same or different than the first diameter, the first and second end each being aligned along a respective longitudinal axis of the plate, and the first and second end each being joined by a middle section which has a width in the direction perpendicular to the respective longitudinal axis, the width being smaller than the first diameter and the second diameter, each of the first tabs including a locking hole for a locking screw, the locking hole having a midpoint and a midline, and each of the second tabs including an ovoid compression slot having a long axis, and each of the compression slots defining a first lateral edge and a second lateral edge which include an inclined shoulder that slopes downward toward the bone facing surface of the plate parallel to the respective long axis of the respective compression slot, each of the midline of the locking hole and the long axis of the compression slot being aligned along the respective longitudinal axis of the plate, and a line connecting the midpoint of the first locking hole and the second locking hole being other than perpendicular to the first or second longitudinal axis;
fixing a locking screw in each of the locking holes;
fixing a non-locking screw in each of the compression slots to cause compression in the associated bone toward the locking hole.

17. A method of fusing bones as set forth in claim 16 wherein a drill guide is used to drill a pilot hole for the non-locking screw and to drill a pilot hole for the non-locking screw.

* * * * *